United States Patent [19] [11] 4,182,762
Preiss [45] Jan. 8, 1980

[54] DIOXOPIPERAZINE DERIVATIVES SUITABLE FOR USE AS MEDICAMENTS AND β-LACTAM ANTIBIOTIC INTERMEDIATES

[75] Inventor: Michael Preiss, Wuppertal, Fed. Rep. of Germany

[73] Assignee: Bayer Aktiengesellschaft, Leverkusen, Fed. Rep. of Germany

[21] Appl. No.: 861,473

[22] Filed: Dec. 16, 1977

[30] Foreign Application Priority Data
Dec. 18, 1976 [DE] Fed. Rep. of Germany ....... 2657559

[51] Int. Cl.² .............. C07D 241/02; C07D 405/02; C07D 409/02
[52] U.S. Cl. ............................. 424/250; 542/420; 542/425; 544/382; 544/385
[58] Field of Search ............... 544/382, 385; 542/420, 542/425; 424/250

[56] References Cited
U.S. PATENT DOCUMENTS

| | | | |
|---|---|---|---|
| 3,183,229 | 5/1965 | Cusic et al. ................... | 544/382 |
| 3,746,704 | 7/1973 | Kollmeyer et al. .............. | 542/420 |
| 3,803,136 | 4/1974 | Schwan et al. ................. | 542/420 |
| 3,830,805 | 8/1974 | Pilgram ........................ | 542/420 |
| 3,903,081 | 9/1975 | Winkelmann .................... | 544/382 |
| 3,978,068 | 8/1976 | Dickore et al. ................ | 542/425 |
| 4,049,650 | 9/1977 | White .......................... | 542/420 |

OTHER PUBLICATIONS
Saikawa et al., Chem Abst. 87, (1977), #102380 #53376 and #53377.
Knobloch et al., Chem. Abstracts 58, col. 2504(b).

*Primary Examiner*—Arthur P. Demers
*Attorney, Agent, or Firm*—Sprung, Felfe, Horn, Lynch & Kramer

[57] ABSTRACT

New dioxo-piperazine derivatives suitable for use as medicaments and β-lactam antibiotic intermediates of the formula

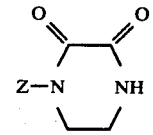

in which
Z is

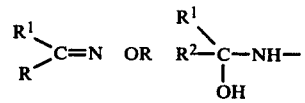

and,
$R^1$ and $R^2$ each independently is hydrogen or various optionally substituted aliphatic, aromatic or heterocyclic radicals or together form an optionally substituted ring,
are formed by reacting
(a) 1-amino-2,3-dioxo-piperazine of the formula

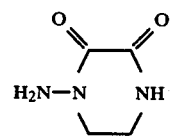

with a compound of the formula

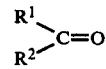

or a hydrate, acetal, ketal, sulphite, hydrogen halide or hydrocyanic acid addition product thereof or,

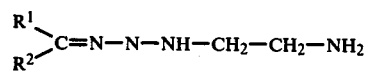 b)

with an oxalic acid ester in the presence of a diluent, thereby to effect cyclization. The new derivatives are anti-virally active and can also be chlorocarbonated with phosgene to form a reactive derivative which can be condensed with the amino group of α-amino penicillins to form a ntibiotics.

12 Claims, No Drawings

DIOXOPIPERAZINE DERIVATIVES SUITABLE FOR USE AS MEDICAMENTS AND β-LACTAM ANTIBIOTIC INTERMEDIATES

The present invention relates to new dioxopiperazine derivatives, processes for their preparation, and their use as medicaments and intermediate products for β-lactam antibiotics.

The present invention provides dioxopiperazine derivatives of the general formula I

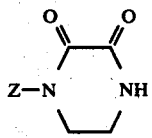

in which Z represents the group

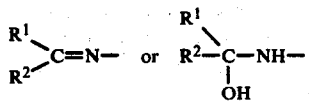

wherein $R^1$ and $R^2$ are identical or different and each denotes hydrogen, an optionally substituted alkyl, alkenyl, cycloalkyl, cycloalkenyl, cycloalkadienyl, aralkyl, aryl or heterocyclyl group, a carboxyl, methoxycarbonyl ethoxycarbonyl, cyano, nitro, or lower alkylcarbonyl group or, —CONH$_2$, —CONHCH$_3$, —CON(CH$_3$)$_2$, —SO$_2$NH$_2$, —SO$_2$—NHCH$_3$ or —SO$_2$N(CH$_3$)$_2$ or $R^1$ and $R^2$, together with the carbon atoms to which they are bonded, form an optionally substituted 3-membered to 7-membered saturated or unsaturated carbocyclic or heterocyclic ring,
and which, where Z represents the group

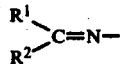

and $R^1$ and $R^2$ are different, can be either in the syn-form or in the anti-form, with respect of the amino group.

The compounds of the invention can be used as intermediate products for the preparation of valuable new antibiotics. Furthermore, the compounds of the invention have an antimicrobial action.

In the above formulae, preferred optionally substituted alkyl groups for the radicals $R^1$ and $R^2$ are straight-chain or branched alkyl with 1 to 6, in particular 1 to 4, carbon atoms. Examples which may be mentioned are optionally substituted methyl, ethyl, n- and i-propyl and n-, i- and t-butyl.

Preferred optionally substituted alkenyl groups for the radicals $R^1$ and $R^2$ are straight-chain or branched alkenyl with 2 to 6, in particular 2 to 4, carbon atoms. Examples which may be mentioned are optionally substituted ethenyl, propen-1-yl, propen-2-yl and buten-3-yl.

Preferred optionally substituted cycloalkyl, cycloalkenyl and cycloalkadienyl groups for the radicals $R^1$ and $R^2$ are mono-, bi- or tri-cyclic groups containing 3 to 10, in particular 3, 5 or 6, carbon atoms. Examples which may be mentioned are optionally substituted cyclopropyl, cyclobutyl, cyclopentyl, cyclopentenyl, cyclohexyl, cyclohexenyl, cyclohexadienyl, cycloheptyl, bicyclo[2.2.1]-heptyl, bicyclo-[2.2.2]-octyl and adamantyl.

Preferred optionally substituted aryl groups for the radicals $R^1$ and $R^2$ are aryl with 6 to 10 carbon atoms in the aryl part. Examples which may be mentioned are optionally substituted phenyl or naphthyl. Substituents in the phenyl ring may be in the o-, m- or p-position. The radicals

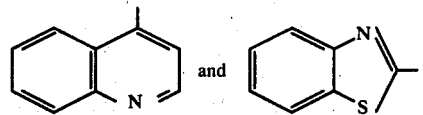

may also be mentioned.

Preferred optionally substituted aralkyl groups for the radicals $R^1$ and $R^2$ are aralkyl which are optionally substituted in the aryl part and/or the alkyl part and have 6 or 10, in particular 6, carbon atoms in the aryl part and preferably 1 to 4, in particular 1 or 2, carbon atoms in the alkyl part, it being possible for the alkyl part to be straight-chain or branched. Examples which may be mentioned are optionally substituted benzyl and phenylethyl.

Preferred optionally substituted heterocyclyl groups for the radicals $R^1$ and $R^2$ are hetero-paraffinic, hetero-aromatic and hetero-olefinic 5-membered to 7-membered, especially 5-membered or 6-membered, rings with preferably 1 to 3, in particular 1 or 2, identical or different hetero-atoms. Suitable hetero-atoms are oxygen, sulphur or nitrogen. Examples which may be mentioned are optionally substituted thienyl, furyl, oxazolyl, isoxazolyl, thiazolyl, isothiazolyl, pyrrolyl, imidazolyl, pyrazolyl, oxdiazolyl, thiadiazolyl, triazolyl, oxtriazolyl, thiatriazolyl, tetrazolyl, pyridyl, pyrazinyl, pyrimidinyl, tetrahydrofuranyl, dioxanyl, pyrrolidinyl, piperidinyl, morpholinyl and 2- and 4-pyronyl.

The alkyl, alkenyl, cycloalkyl, cycloalkenyl, cycloalkadienyl, aryl and aralkyl groups of radicals $R^1$ and $R^2$ can carry one or more, preferably 1 to 3, in particular 1 or 2, identical or different substituents preferably selected from the radicals used in the following definition of $R^3$. It is particularly preferred that the said radicals $R^1$ and $R^2$ be unsubstituted or contain one substituent.

The heterocyclyl groups of the radicals $R^1$ and $R^2$ can carry one or more, preferably 1 to 3, in particular 1 or 2, identical or different substituents preferably selected from the radicals listed in the following definition of $R^4$. It is particularly preferred that the heterocyclyl $R^1$ and $R^2$ be unsubstituted or contain one substituent $R^4$.

In the statements which follow, the expression "lower alkyl" in all cases, even in combination with other atoms or groups (for example lower alkoxy, HCON—(lower alkyl) and the like), denotes straight-chain or branched alkyl with preferably 1 to 6, in particular 1 to 4, carbon atoms. Examples which may be mentioned are optionally substituted methyl, ethyl, n- and i-propyl and n-, i- and t-butyl. "Lower alkyl" groups can be substituted by 1 to 5, in particular 1 to 3, identical or different halogen atoms, the halogen atoms preferably being fluorine, chlorine and bromine, especially fluorine and chlorine. Examples which may be mentioned are trifluoromethyl, chloro-di-fluoromethyl, bromomethyl, 2,2,2-tri-fluoroethyl and pentafluoroethyl.

$R^3$ preferably denotes halogen, in particular fluorine, chlorine and bromine; amino; mono-lower alkylamino, preferably methylamino or ethylamino, especially methylamino; di-lower alkylamino, preferably dimethylamino or diethylamino, especially dimethylamino; pyrrolidyl; piperidyl; NCO—NH—; lower alkyl—CO—NH—, preferably CH₃—CO—NH—; H—CO—N(lower alkyl)—, preferably H—CO—N(CH₃)— or H—CO—N(C₂H₅)—; lower alkyl—CO—N—(lower alkyl)—, preferably CH₃—CO—N(CH₃)—; (lower alkyl)₂—C=N—; lower alkyl—SO₂—NH—, preferably CH₃—SO₂—NH— or C₂H₅—SO₂—NH—, especially CH₃—SO₂—NH—; lower alkyl—SO₂—N(lower alkyl)—, preferably CH₃—SO₂—N(CH₃)—; HO—SO₂—NH—; HO—SO₂—N(lower alkyl)—, preferably HO—SO₂—N(CH₃)— or HO—SO₂—N(C₂H₅)—; amidino;

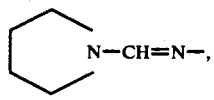

guanido, nitro, azido, hydroxyl, lower alkyl-oxy, preferably CH₃—O—C₂H₅—O—, especially CH₃O—; H—CO—O—, lower alkyl—CO—O—, preferably CH₃—CO—O, C₂H₅—CO—O— or (CH₃)₃C—CO—O—; lower alkyl—O—CO—O—, preferably CH₃—O—CO—O—, C₂H₅—O—CO—O— or (CH₃)₃C—O—CO—O—; H₂N—CO—O; lower alkyl—NH—CO—O—, preferably CH₃—NH—CO—O— or C₂H₅—NH—CO—O—; (lower alkyl)₂N—CO—O—, preferably (CH₃)₂N—CO—O—, (C₂H₅)₂N—CO—O—,

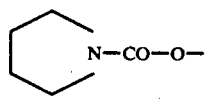

or H₂N—SO₂—O—; lower alkyl—NH—SO₂—O—, preferably CH₃—NH—SO₂—O— or C₂H₅—NH—SO₂—O—; (lower alkyl)₂N—SO₂—O—, preferably (CH₃)₂ N—SO₂—O—, (C₂H₅)₂ N—SO₂—O—; HOOC— or H₂N—CO—; (lower alkyl)₂N—CO—, in particular (CH₃)₂N—CO— and (C₂H₅)₂N—CO—; OHC—; HO—SO₂—O— or HS—; lower alkyl—S—, preferably CH₃—S—, CF₃—S—, C₂H₅—S— or (CH₃)₂CH—S—; lower

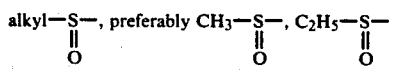

or HO₃S—; lower alkyl—SO₂—, preferably CH₃—SO₂—, CF₃SO₂— or C₂H₅—SO₂—; the group H₂N—SO₂—; lower alkyl—NH—SO₂—, preferably CH₃—NH—SO₂— or C₂H₅—NH—SO₂—; (lower alkyl)₂N—SO₂—, preferably (CH₃)₂ N—SO₂— or (C₂H₅)₂ N—SO₂—;

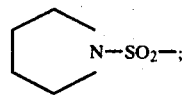

the group HO—SO₂—S—; straight-chain or branched alkyl with 1 to 6 carbon atoms, in particular methyl, ethyl, propyl, isopropyl, n-butyl, sec.-butyl or tert.-butyl, preferably methyl; 2-furyl and phenyl or phenoxy.

In the case where $R^4$ is on one or more carbon atoms in the heterocyclyl $R^1$ and $R^2$, $R^4$ preferably denotes lower alkyl, preferably methyl, ethyl or isopropyl, especially methyl; cycloalkyl with 3 to 7, preferably 3 to 6, carbon atoms, in particular cyclopropyl; the group trifluoromethyl; halogen, preferably fluorine, chlorine or bromine; nitro or amino; lower alkylamino, preferably CH₃—NH— or C₂H₅—NH—; di-lower alkylamino, preferably (CH₃)₂N— or (C₂H₅)₂N—; formylamino; acetylamino; CH₃—O—CO—NH— or C₂H₅O—CO—NH—; CH₃—SO₂—NH—; hydroxyl; methoxy or ethoxy; methylthio or ethylthio; CH₃—SO₂—; CH₃—SO—; lower alkyl—NH—SO₂, preferably CH₃—NH—SO₂—; lower alkyl-oxy—CH₂—, in particular CH₃O—CH₂— and C₂H₅O—CH₂—; heterocyclyl-aldimino (definition of heterocyclyl as for $R^1$ and $R^2$), in particular furyl-2-aldimino; alkenyl (definition as for $R^1$ and $R^2$), in particular allyl; and

the groups HOOC; HO₃S—; lower alkyl-NHSO₂—, in particular CH₃—NH—SO₂—; (lower alkyl)₂—NSO₂—, in particular (CH₃)₂NSO₂; HCO—; lower alkyl—CO—, preferably CH₃—CO—; lower alkyl—O—CO—, preferably CH₃O—CO— or C₂H₅O—CO—; and —CN; lower alkyl—O—CO—CH₂—, preferably CH₃—O—COCH₂— or C₂H₅OCOCH₂—; (lower alkyl—O)₂-CH—, preferably (C₂H₅O)₂CH—; HO—lower alkyl, preferably HO—CH₂—, (CH₃)₂C(OH)— and

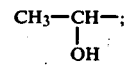

and thienyl, furyl, oxazolyl, isoxazolyl, thiazolyl, isothiazolyl, pyrrolyl, imidazolyl, pyrazolyl, oxdiazolyl, thiadiazolyl, triazolyl, oxtriazolyl, thiatriazolyl, tetrazolyl, pyridyl, pyrazinyl, pyrimidinyl, tetrahydrofuranyl, dioxanyl, pyrrolidinyl, piperidinyl or morpholinyl, preferably furyl.

In the case where $R^4$ is a substituent on one or more nitrogen atoms in a nitrogen-containing heterocyclyl $R^1$ and $R^2$, $R^4$ preferably denotes lower alkyl, preferably methyl, ethyl, propyl or isopropyl, especially methyl and ethyl; the group —C=N; —CHO; —COO—lower alkyl, preferably —COO—CH₃, —COOC₂H₅, —COOCH(CH₃)₂ or —COO—C(CH₃)₃; —CO—NH₂; —CO—NH-lower alkyl, preferably —CO—NH—CH₃, —CO—NH—C₂H₅ or —CO—NH—CH(CH₃)₂; and —CO—lower alkyl, preferably —CO—CH₃, —CO—C₂H₅ or —CO—CH(CH₃)₂.

The rings which can be formed by $R^1$ and $R^2$, together with the carbon atoms to which they are bonded, may be saturated or unsaturated. Unsaturated rings contain preferably 1 or 2 double bonds. The rings can contain 1 or more, preferably 1 or 2, in particular 1, hetero-atom or hetero-group. Hetero-atoms which may be mentioned are oxygen, sulphur and/or nitrogen. Examples of hetero-groups which may be mentioned are the SO₂ group and the lower alkyl—N— group and in the case of 6-membered rings, a hetero-atom or a hetero-group is preferably in the 4-position (relative to the carbon atom to which R¹ and R² are bonded). Particularly preferred rings which may be mentioned are:

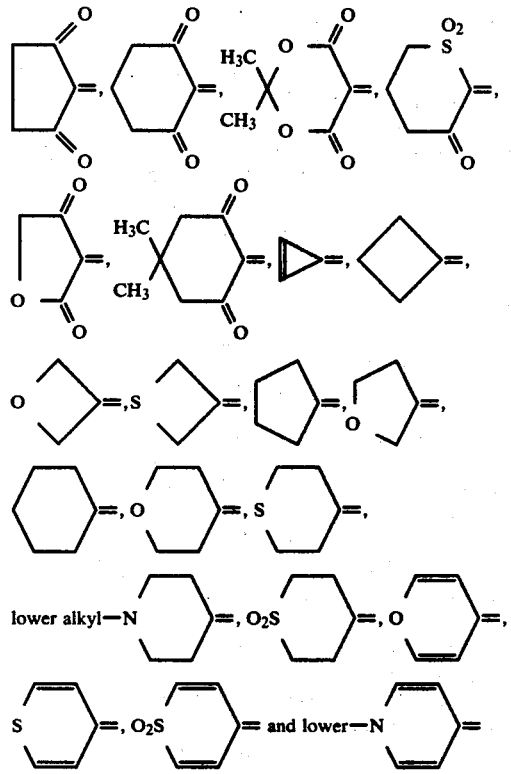

The rings which are formed by R¹ and R², together with the carbon atoms to which they are bonded, can contain one or more, preferably 1 to 3, in particular 1 or 2, identical or different substituents R⁵. R⁵ preferably denotes halogen, preferably fluorine, chlorine or bromine; hydroxyl, lower alkoxy, preferably methoxy and ethoxy; lower alkythio, preferably methylthio or ethylthio; amino; lower alkylamino, preferably CH₃—NH or C₂H₅—NH—; di-lower alkylamino, preferably dimethylamino and diethylamino; the groups —CN; —COOH; —COOCH₃ or COOC₂H₅; and straight-chain or branched lower alkyl, preferably methyl and ethyl.

Particularly preferentially, at least one of the radicals R¹ and R² represents hydrogen.

Particularly preferentially, Z represents the group

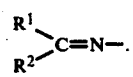

Compounds which contain the radical

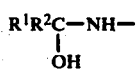

are formed when this radical is already contained in the compounds of the formula I or can be formed when the reaction is carried out in solvents containing water.

Very particularly preferred compounds of the formula I are those in which the definition of the radicals is as follows:

Z represents the groups

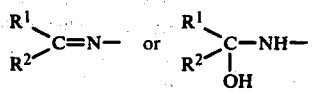

wherein
R¹ denotes hydrogen and
R² represents a straight-chain or branched alkyl radical with 1 to 6 carbon atoms or a phenyl radical which is optionally substituted by halogen, preferably fluorine, chlorine and bromine, alkyl with 1 to 4 carbon atoms, in particular methyl, alkoxy with 1 to 4 carbon atoms, preferably methoxy, nitro, cyano, hydroxyl, alkylsulphonyl with 1 to 4 carbon atoms, preferably methylsulphonyl or methoxycarbonyl, or represents a furyl, thienyl or isoxazolyl radical which is optionally substituted by halogen, preferably chlorine or bromine, or alkyl with 1 to 4 carbon atoms, preferably methyl. Examples of new compounds which may be mentioned are:

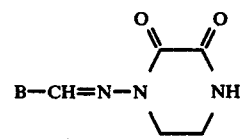

wherein

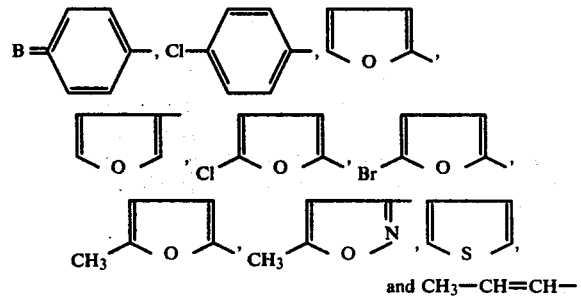

and CH₃—CH=CH—

Furthermore, it has been found that the new compounds of the formula I are obtained when 1-amino-2,3-dioxopiperazine (II)

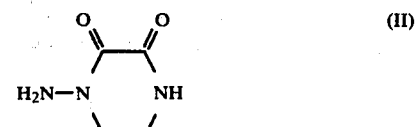

is reacted with compounds of the formula III

in which $R^1$ and $R^2$ have the meaning indicated above, or their hydrate or acetal forms or ketal forms as well as sulphite, hydrogen halide or hydrocyanic acid addition products, optionally in the presence of an agent which binds the water of reaction, a diluent and an acid catalyst.

In order to obtain compounds of the general formula I, the procedure followed can also equally well be to react β-aminoethyl hydrazine, the preparation of which is known from DAS (German Published Specification) NO. 1,108,233, with compounds of the formula III to give hydrazones of the formula IV

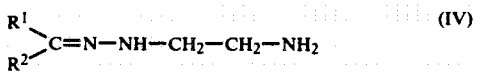

in which $R^1$ and $R^2$ have the meaning indicated above, and to subject these to a condensation reaction, with cyclisation, with oxalic acid esters, preferably oxalic acid dimethyl ester or diethyl ester, optionally in the presence of a diluent.

The following equation illustrates, by way of example, the last-mentioned process:

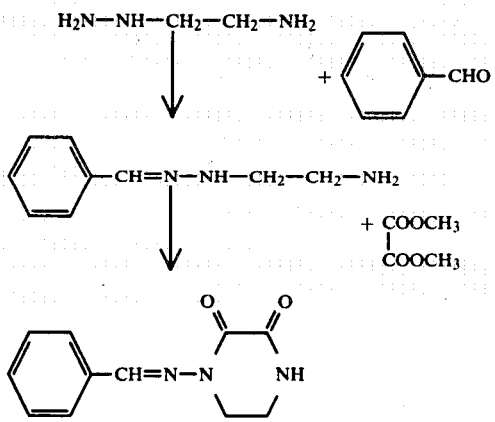

The starting material 1-amino-2,3-dioxo-piperazine (II) is obtained, for example, according to the following equation (compare also J. Amer. Chem. 78, 5349 (1956) and DT-AS (German Published Specification) No. 1,108,233 (1959)):

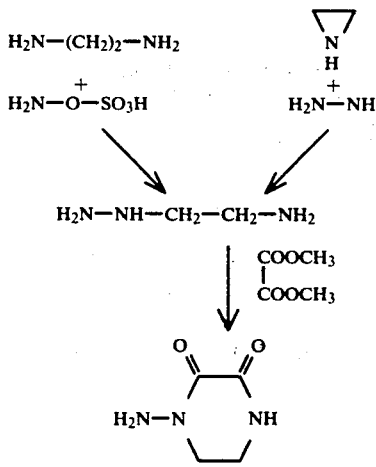

All the customary agents which bind water physically and/or chemically can be used as the water-binding agent in the process according to the invention. Such agents are: molecular sieves, anhydrous alkali metal sulphates and perchlorates and alkaline earth metal sulphates and perchlorates and alkaline earth metal sulphates and perchlorates, oxides, such as boron trioxide, magnesium oxide, calcium oxide, aluminium oxide and silica gel, and carbodiimides. However, the water reaction can also be equally well distilled off azeotropically, for example with benzene. The reaction can also optionally be equally well carried out without a water-binding agent.

All the proton acids and acid ion exchangers can be used as the acid catalysts in the process according to the invention. Sulphuric acid, p-toluenesulphonic acid and ion exchangers having acid groups are preferred. The reaction can also optionally be carried out without a catalyst.

All the organic solvents can be used as the diluent. Dimethylformamide, dimethylsulphoxide, lower alcohols, acetonitrile, dioxane, tetrahydrofurane, pyridine, benzene or acetic acid are preferred.

The reaction temperatures can be varied within a relatively wide range. In general, the reaction is carried out between about $-20°$ C. and about $+150°$ C., preferably between about $+20°$ C. and $120°$ C. However, as in most chemical reactions, in principle higher or lower temperatures can also be used.

The reaction can be carried out under normal pressure, but also under reduced or increased pressure. In general, the reaction is carried out under normal pressure.

In carrying out the process according to the invention, the proportions of reactants of the formula II and III can be varied within wide limits without the result being adversely influenced. For example, the starting materials can be reacted with one another in equimolar amounts. However, it can be appropriate to use one of the two reactants in excess in order to make the purification of the desired compound or its preparation in a pure form easier and to increase the yield.

The substances according to the invention have an action against a number of micro-organisms. With their aid it is possible to combat viruses and to prevent, alleviate and/or cure diseases caused in humans and animals by these pathogens.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile or isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third, or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble or water-insoluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, ispropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, the solutions and emulsions should be sterile, and, if appropriate, bloodisotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention preferably contain about 0.1 to 99.5, more preferably from about 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted, by virtue of their shape or packaging, for medical administration and may be, for example, any of the following: tablets, (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 5 mg to 10 g of active ingredient.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above-mentioned diseases in human and non-human animals, which comprises administering to the animals a compound of the invention alone or in admixture with a diluent or in the form of a medicament according to the invention.

It is evisaged that these active compounds will be administered perorally, parenterally (for example intramuscularly, intraperitoneally or intravenously), rectally or locally.

In general it has proved advantageous to administer amounts of from 1 mg to 500 mg/kg of body weight per day to achieve effective results. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some cases suffice to use less than the above-mentioned minimum dosage rate, whilst other cases the upper limit mentioned must be exceeded to achieve the desired results. Where larger amounts are administered in can be advisable to divide these into several individual administrations over the course of the day.

The substances according to the invention can also be employed as intermediate products for the preparation of new, valuable, β-lactam antibiotics.

For this, the dioxopiperazine derivatives of the formula I are converted, by reaction with compounds of the formula V

W—CE—W (V)

in which
W denotes halogen, preferably chlorine, azide or one of the groups

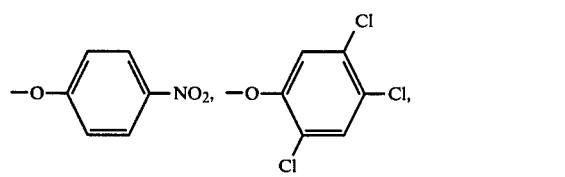

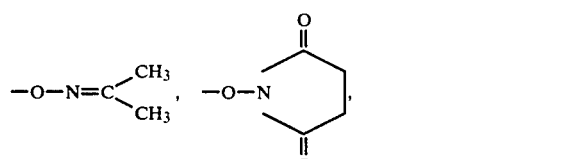

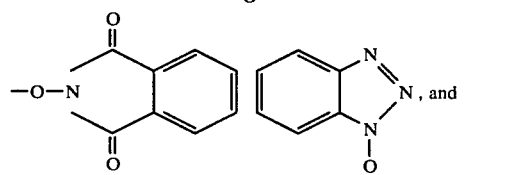

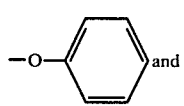

E represents oxygen or sulphur, into compounds of the formula IV

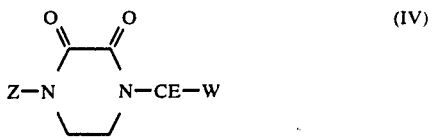

in which Z, E and W have the meaning indicated above.

In order to prepare the compounds of the formula IV, in which Z and E have the meaning indicated above and W represents chlorine, the compounds of the formula I are reacted with phosgene or thiophosgene in organic solvents, such as, for example, tetrahydrofurane, dioxane, ethyl acetate, benzonitrile, pyridine, dimethylformamide, acetonitrile or chloroform, and in the presence of, for example, a molar amount of a base, such as, for example, triethylamine, sodium hydride, 4-dimethylamino-pyridine or sodium amide, or also in the absence of a base, at temperatures from about $-5°$ to about $25°$ C. and the reaction product is isolated and purified by methods which are generally customary.

If W is not halogen, the compounds of the formula VI can be easily prepared by customary methods from compounds of the general formula IV in which W is halogen, by reaction with compounds of the general formula H-W, in which W has the meaning indicated above (with the exception of halogen), in the presence of a base, such as triethylamine, in inert organic solvents, such as tetrahydrofurane, or mixtures of water and inert organic solvents, such as chloroform.

New, valuable β-lactam antibiotics are thus obtained when compounds of the general formula VII

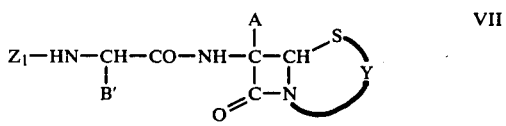

in which
B′ represents optionally substituted phenyl, cyclohexenyl, cyclohexadienyl or thienyl,
A represents hydrogen or methoxy,
Y represents the groups

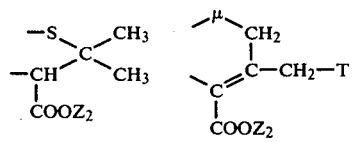

in which the carbon atoms which carried the carboxyl group is bonded to the nitrogen atom of the β-lactam ring and T represents hydrogen, alkyl—CO—O— hydroxyl-, pyridinium, amino-pyridinium, carbamoyloxy, azido, cyano, thiocarbamoylthio, the group —S-phenyl, which can be substituted, or the group —S—Het, in which
Het represents an optionally substituted heterocyclic 5-membered or 6-membered ring;
U represents oxygen, sulphur or the —CH$_2$— group; and
Z$_1$ and Z$_2$ are identical or different and represent hydrogen or a silyl radical,
or their salts are reacted with compounds of the formula VI in the presence of solvents, optionally in the presence of a base, in a temperature range from about $-20°$ C. to +50° C. and, if appropriate after splitting off the silyl groups, the resulting β-lactam antibiotics are converted, if desired, into their non-toxic, pharmaceutically acceptable salts.

Diluents which can be used for the process according to the invention are all the inert organic solvents as well as water and mixtures of water and organic solvents.

If compounds of the general formula VII in which $Z_1$ and $Z_2$ represent hydrogen or $Z_1$ represents hydrogen and $Z_2$ represents a silyl group which is relatively stable towards solvolysis or $Z_1$ and $Z_2$ represent silyl groups which are relatively stable towards solvolysis (for example silyl groups of the types $Si(CH_3)(OCH_3)_2$ and $Si(CH_3)_2(OCH_3)$) are used as the starting materials for the synthesis of the penicillins according to the invention, these reactions can be carried out in any desired mixtures of water with those organic solvents which are miscible with water, such as ketones, for example acetone, cyclic ethers, for example tetrahydrofurane or dioxane, nitriles, for example acetonitrile, formamides, for example dimethylformamide, dimethylsulphoxide or alcohols, for example isopropanol. In this procedure, the pH of the reaction mixture is kept in a pH range from about 1.5 to 9.5, for example between about pH 6.5 and 8, by adding bases or using buffer solutions. However, the reaction according to the invention can also be carried out in another pH range, for example between about 4.5 and 9, or about pH 2 to 3. Furthermore, it is possible to carry out the reaction in solvents which are immiscible with water, for example halogenated hydrocarbons, such as chloroform or methylene chloride, with the addition of bases, preferably triethylamine, diethylamine or N-ethylpiperidine. Moreover, the reaction can be carried out in a mixture of water and a solvent which is immiscible with water, such as ethers, for example diethyl ether, halogenated hydrocarbons, for example chloroform or methylene chloride, carbon disulphide, ketones, for example isobutyl methyl ketone, esters, for example ethyl acetate, or aromatic solvents, for example benzene, it being appropriate to stir the reaction mixture vigorously and to keep the pH value in a range from about pH 1.5 to about 9.5, for example between 4.5 and 9.0 or between 2.0 and 3.0, by adding bases or using buffer solutions. However, it is also possible to carry out the reaction in water alone in the absence of organic solvents and in the presence of an organic or inorganic base or with the addition of buffer substances.

If compounds of the general formula VII in which $Z_1$ denotes hydrogen and $Z_2$ denotes a silyl group which is not very stable towards solvolysis or in which $Z_1$ and $Z_2$ denote silyl groups which are not very stable towards solvolysis (for example of the type $Si(CH_3)_3$) are used as the starting material for the process according to the invention and they are reacted with compounds of the general formula VII, in general the reaction is appropriately carried out in solvents which are anhydrous and free from hydroxyl groups, for example in halogenated hydrocarbons, for example methylene chloride or chloroform, benzene, tetrahydrofurane, acetone or dimethylformamide and the like. It is not necessary to add bases here, but it can be advantageous in individual cases in order to improve the yield and purity of the products. However, the reverse effect is also possible. The bases optionally added must be either tertiary aliphatic or aromtic amines, such as pyridine or tertiary alkylamines, for example triethylamine or secondary amines which, because of steric hindrance, are difficult to acylate, such as dicyclohexylamine. The particular optimum bases can be easily determined by any of those skilled in the art.

The amount of bases used is determined, for example, by the particular pH value it is desired to maintain. Where a pH measurement and adjustment is not carried out or, because of the absence of sufficient amounts of water in the diluent, it is not possible or not meaningful in the case where compounds of the general formula VII in which $Z_1$ and $Z_2$ is hydrogen are used, preferably about 1 to 2.5, in particular about 1.5 to 2.0, molar equivalents of base are employed. In the case where compounds of the general formula VII in which $Z_1$ is hydrogen and $Z_2$ is a silyl group, or in which $Z_1$ and $Z_2$ are silyl groups are used, either no base is used or preferably about 0,5 to 2, in particular about 1, molar equivalent of base is used.

In principle, all the organic and inorgaic bases customarily used in organic chemistry, such as alkali metal hydroxides and alkaline earth metal hydroxides, alkaline earth metal oxides, alkali metal carbonates and alkaline earth metal carbonates and bicarbonates, ammonia, primary, secondary and tertiary aliphatic and aromatic amines and heterocyclic bases, can be used as the bases. Examples which may be mentioned are sodium hydroxide, potassium hydroxide and calcium hydroxide, calcium oxide, sodium carbonate and potassium carbonate, sodium bicarbonate and potassium bicarbonate, ethylamine, methylethylamine, triethylamine, hydroxyethylamine, aniline, pyridine and piperidine. However, when silylated starting materials are used the limitations above with respect to the nature of the bases should be observed.

All the customary buffer mixtures can be used as buffer systems, for example phosphate buffers, citrate buffers and tris-(hydroxymethyl)amino-methane buffers.

The reaction temperatures can be varied within a relatively wide range. In general, the reaction is carried out between about −20° and +50° C., preferably between about 0° and +20° C.

The reaction can be carried out under normal pressure, but also under reduced or increased pressure. In general, the reaction is carried out under normal pressure.

In carrying out the processes according to the invention, the reactants can be reacted with one another in equimolar amounts. However, it can be appropriate to use one of the two reactants in excess in order to make the purification of the desired penicillin or its preparation in a pure form easier and to increase the yield.

For example, it is possible to employ the reactants of the general formula VII in an excess of about 0.1 to about 1, preferably of 0.1 to 0.3, molar equivalents, relative to the starting compound of the formula VI, and thereby to achieve less decomposition of the reactants of the general formula VI in a solvent mixture containing water. Because of their good solubility in aqueous mineral acids, the excess of the reactants of the general formula VII can be easily removed during the working up of the reaction mixture.

On the other hand, however, the reactants of the general formula VI can also be advantageously employed in an excess of, for example, about 0.1 to about 1.5, preferably about 0.1 to 1.0, molar equivalent. The reactants of the general formula VII are thereby better utilised and the decomposition of the reactants of the general formula IV, which proceeds as a side-reaction in solvents containing water, is compensated. Since the compounds of the general formula VI added in excess are rapidly converted in water into neutral nitrogen-containing heterocyclic compounds which can be easily removed, the purity of the β-lactam antibiotics is hereby scarcely impaired. Thus, in general, in each case the less valuable reactant is used in excess.

Working up of the reaction mixture in order to prepare the β-lactam antibiotics according to the invention, and their salts, is carried out in the manner which is generally customary and known in penicillin chemistry, for example by removing the solvent and reprecipitating or recrystallising the residue. The salts can be particularly easily precipitated from ethereal solutions. Thus the new β-lactam antibiotics can be particularly favourably precipitated as sodium salts from an ethereal solution with the aid of sodium 2-ethylhexanoate.

If D-α-amino-benzylpenicillin and 1-furfurylideneamino-2,3-dioxopiperazine are used as the starting materials, the course of the reaction can be represented by the following reaction scheme.

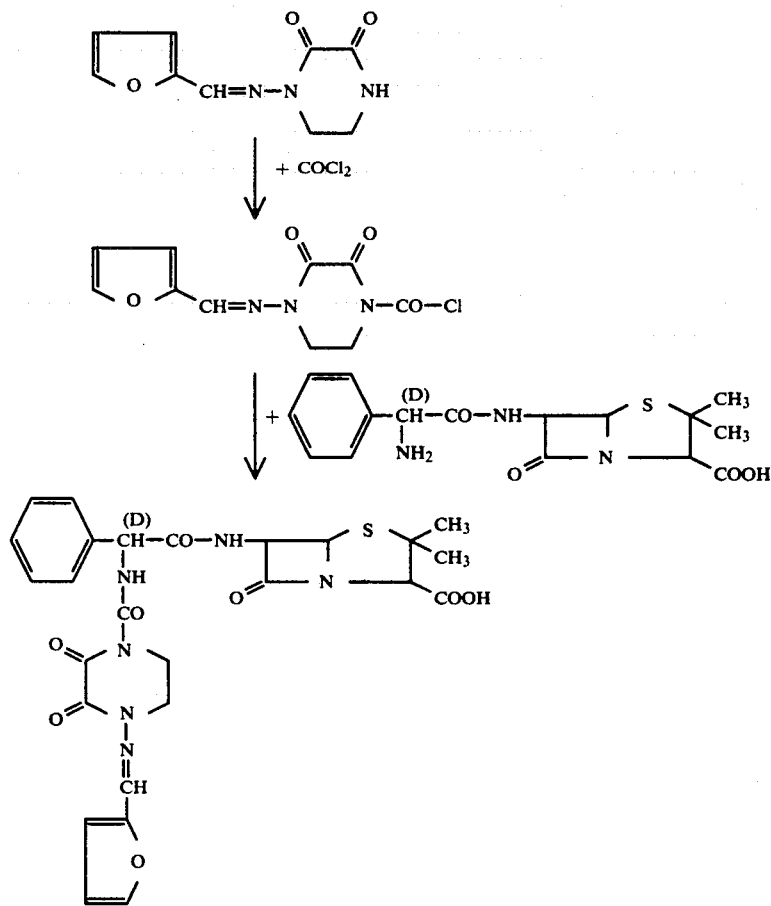

Amoxicillin and cephaloglycine, in particular, can also be reacted in the manner above to give valuable, new β-lactam antibiotics.

The β-lactam antibiotics according to the invention display a powerful antimicrobial action, coupled with low toxicity and good tolerance. These properties enable them to be used as active compounds in medicine and as substances for preserving inorganic and organic materials, in particular organic materials of all kinds, for example polymers, lubricants, paints, fibres, leather, paper and timber, foodstuffs and water.

The β-lactam antibiotics according to the invention are active against a very broad spectrum of micro-organisms. With their aid it is possible to combat, for example, Gram-negative and Gram-positive bacteria and bacteria-like micro-organisms and to prevent, alleviate and/or cure diseases caused by these pathogens.

The β-lactam antibiotics according to the invention are particularly active against bacteria and bacteria-like micro-organisms. They are therefore particularly suitable for the prophylaxis and chemotherapy of local and systemic infections, caused by these pathogens, in human medicine and veterinary medicine.

For example, local and/or systemic diseases which are caused by the following pathogens or by mixtures of the following pathogens can be treated and/or prevented:

Micrococcaceae, such as Staphylococci, for example *Staphylococcus aureus, Staph. epidermidis, Staph. aerogenes* and *Gaffkya tetragena* (Staph.=Staphylococcus);

Lactobacteriaceae, such as Streptococci, for example *Streptococcus pyogenes,* α- and β-haemolysing Streptococci, non (γ-)-haemolysing Streptococci, *Str. viridans, Str. faecalis* (Enterococci), *Str. agalactiae, Str. lactis, Str. equi, Str. anaerobis* and *Diplococcus pneumoniae* (Pneumococci) (Str.=Streptococcus);

Neisseriaceae, such as Neisseria, for example *Neisseria gonorrhoeae* (Gonococci), *N. meningitidis* (Meningococci), *N. catarrhalis* and *N. flava* (N.=Neisseria);

Corynebacteriaceae, such as Corynebacteria, for example *Corynebacterium diphtheriae, C. pyrogenes, C. diphtheroides, C. acnes, C. parvum, C. bovis, C. renale, C. ovis* and *C. murisepticum*, Listeria bacteria, for example *Listeria monocytogenes*, Erysipelothrix bacteria, for example *Erysipelothrix insidiosa* and Kurthia bacteria, for example *Kurthia zopfii* (C.=Corynebacterium);

Enterobacteriaceae, such as Escherichiae bacteria of the Coli group, Escherichia bacteria, for example *Escherichia coli*, Enterobacter bacteria, for example *E. aerogenes* and *E. cloacae*, Klebsiella bacteria, for example *K. pneumoniae* and *K. ozaenae*, Erwiniae, for example Erwinia spec., Serratia, for example *Serratia marcescens* (E.=Enterobacter) (K.=Klebsiella), Proteae bacteria of the Proteus group, Proteus, for example *Proteus vulgaris, Pr. morganii, Pr. rettgeri* and *Pr. mirabilis* (Pr.=Proteus), Providencia, for example Providencia sp., Salmonelleae, Salmonella bacteria, for example salmonella paratyphi A and B, *S. typhi, S. enteritidis, S. cholerae suis* and *S. typhimurium* (S.=Salmonella), and Shigella bacteria, for example *Shigella dysenteriae, Sh. ambigua, Sh. flexneri, Sh. boydii* and *Sh. sonnei* (Sh.=Shigella);

Pseudomonadaceae, such as Pseudomonas bacteria, for example *Pseudomonas aeruginosa* and *Ps. pseudomallei* (Ps.=Pseudomonas), and Aeromonas bacteria, for example *Aeromonas liquefaciens* and *A. hydrophila* (A.=Aeromonas);

Spirillaceae, such as Vibrio bacteria, for example *Vibrio cholerae, V. proteus* and *V. fetus* (V.=Vibrio), and Spirillum bacteria, for example *Spirillum minus*;

Parvobacteriaesae or Brucellaceae, such as Pasteurella bacteria, for example *Pasteurella multocida, Past. pestis* (Yersinia), *Past. pseudotuberculosis* and *Past. tularensis* (Past.=Pasteurella), Brucella bacteria, for example *Brucella abortus, Br. melitensis* and *Br. suis* (Br.=Brucella), Haemophilus bacteria, for example *Haemophilus influenzae, H. ducreyi, H. suis, H. canis* and *H. aegypitcus* (H.=Haemophilus), Bordetella bacteria, for example *Bordetella pertussis* and *B. bronchiseptica* (B.=Bordetella) and Moraxella bacteria, for example *Moraxella lacunata*;

Bacteroidacea, such as Bacteroides bacteria, for example *Bacteroides fragilis* and *B. serpens* (B.=Bacteroides), Fusiforme bacteria, for example *Fusobacterium fusiforme* and Sphaerophorus bacteria, for example *sphaerophorus necrophorus, Sph. nectroticus* and *Sph. pyrogenes* (Sph.=Sphaerophorus);

Bacillaceae, such as aerobic spore-forming Bacillaceae, for example *Bacillus anthracis, B. subtilis* and *B. cereus* (B.=Bacillus), anaerobic spore-forming Clostridia, for example *Clostridium perfringens, Cl. septicium, Cl. oedematiens, Cl. histolyticum, Cl. tetani* and *Cl. botulinum* (Cl.=Clostridium);

Spirochaetaceae, such as Borrelia bacteria, for example *Borrelia recurrentia* and *B. vincentii* (B.=Borrelia), Treponema bacteria, for example *Treponema palladium, Tr. pertinue* and *Tr. carateum* (Tr.=Treponema) and Leptospira bacteriia, *Leptospira interrogans*, for example *Leptospira icterohaemorrhagiae, L. canicola, L. grippotyphosa, L. pomona, L. mitis* and *L. bovis* (L.=Leptospira).

The above list of pathogens is purely illustrative and is in no way to be interpreted as restrictive.

Examples which may be mentioned of diseases which can be prevented, alleviated and/or cured by the active compounds according to the invention are: diseases of the respiratory passages and of the pharyngeal cavity, otitis, pharyngitis, pneumonia, peritonitis, pyelonephritis, cystitis, endocarditis, systemic infections, bronchitis and arthritis.

The preparation of individual compounds of the invention is described in the following Examples.

Explanation of the abbreviations used in the examples:

pts. by wt.=parts by weight
pts. by vol.=parts by volume
hr., hrs.=hour, hours
THF=tetrahydrofurane
abs.=absolute
decomp. pt.=decomposition point
RT=room temperature In the NMR spectra:
s=singlet
m=multiplet
d=doublet
dd=doublet of doublets
t=triplet
AB=AB system
$A_2B_2 = A_2B_2$ system

EXAMPLE 1

Preparation of starting material

1-Amino-2,3-dioxopiperazine

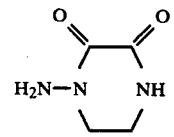

A solution of 5.0 pts. by wt. of (2-amino-ethyl)-hydrazine in 50 pts. by vol. of abs. methanol and a solution of 7.8 pts. by wt. of oxalic acid dimethyl ester in 50 pts. by vol. of abs. methanol are added dropwise, very slowly, at the same time and uniformly, to 50 pts. by vol. of abs. methanol at 50°–60° C., whilst stirring vigorously. After the dropwise addition has ended, the mixture is stirred for a further 1 hr. at this temperature. Thereafter, the white precipitate which has formed is filtered off and the filtrate is concentrated. The residue is recrystallised from methanol/water. 4.8 pts. by wt. of 1-amino-2,3-dioxopiperazine of decomp. pt. 240°–243° C. are obtained.

IR(KBr): 3309, 3238, 1693, 1655, 1585, 1474, 1435, 1366 1297, 1218, 1104, 1001, 944, 921, 716 and 669 cm$^{-1}$.

NMR (D$_2$O): 4.65 (3 exchangeable protons), A$_2$B$_2$ 3.82 and 3.66 (4H) ppm, ($\delta$).

Mass spectrum: m/e 129.

Molecular weight: 129.1 calculated: C 37.21; H 5.46; N 32.55. found: C37.2; H 5.4; N 32.3.

EXAMPLE 2

1-Benzylideneamino-2,3-dioxo-piperazine 1.3 pts. by wt. of 1-amino-2,3-dioxo-piperazine, 1.3 pts. by wt. of benzaldehyde and 7 pts. by vol. of glacial acetic acid are warmed to 90° for 90 minutes and then left at 5° for 30 minutes. The precipitate is filtered off, washed first with 3 pts. by vol. of glacial acetic acid and then with three times 10 pts. by vol. of ethyl acetate and dried over P$_2$O$_5$. 1.75 pts. by wt. (81.8% ) of 1-benzylideneamino-2,3-dioxo-piperazine of melting point 236°–240° C. are obtained.

IR(KBr): 3220, 3110, 2950, 2910, 1685, 1445, 1400, 1360, 1190, 1100, 755 and 695 cm$^{-1}$.

NMR(d₆-DMSO): s (broad) 8.83 (1H), s 8.47 (1H), m centered at 7.85 and m centered at 7.51 (together 5H), A₂B₂ 4.00 and 3.57 (4H) ppm (δ).

Mass spectrum: m/e 217

Molecular weight: 217.2 calculated: C 60.83; H 5.11; N 19.34. found: C 60.8; H 5.2; N 19.0.

EXAMPLE 3

1-Benzylideneamino-2,3-dioxopiperazine

A solution of 14.1 pts. by wt. of freshly distilled benzaldehyde in 30 pts. by vol. of abs. THF is added dropwise to a solution of 10.0 pts. by wt. of (2-amino-ethyl)-hydrazine in 50 pts. by vol. of abs. THF. 6 pts. by wt. of magnesium sulphate are then added and the mixture is stirred overnight at RT. The THF is stripped off and the residue is taken up in 200 pts. by vol. of abs. methanol and 15.5 pts. by wt. of oxalic acid dimethyl ester are added. After stirring for 2 days at RT, a small amount of insoluble material is filtered off and the filtrate is concentrated and recrystallised from acetonitrile. 1.4 pts. by wt. of 1-benzylideneamino-2,3-dioxopiperazine of melting point 231°-234° C. are obtained.

EXAMPLE 4

1-Furfurylideneamino-2,3-dioxo-piperazine 2.3 pts. by wt. of furfural, 2.6 pts. by wt. of 1-amino-2,3-dioxo-piperazine and 10 pts. by vol. of glacial acetic acid are warmed to 90° for 30 minutes and thereafter left for 3 hrs. at RT, whereupon crystallisation occurs. The precipitate is filtered off, washed first with 5 pts. by vol. of glacial acetic acid and then twice with 10 pts. by vol. of ethyl acetate each time and dried over potassium hydroxide. 4.0 pts. by wt. (96.6%) of 1-furfurylideneamino-2,3-dioxo-piperazine of melting point 193°-7° are obtained.

IR(KBr): 3210, 3110, 1675 (broad), 1615, 1475, 1410, 1355, 1285, 1180, 1000 and 815 cm⁻¹.

NMR(d₆DMSO): t 8.93 (1H), s 8.62 (1H), d 7.95 (1H), d 7.08 (1H), dd 7.08 (1H), A₂B₂ 4.00 and 3.59 (4H) ppm (δ).

Mass spectrum: m/e 207

Molecular weight: 207.2 calculated: C 52.17; H 4.38; N 20.28. found: C 52.1; H 4.2; N 20.0.

EXAMPLE 5

1-(5-Methyl-furfurylideneamino)-2,3-dioxo-piperazine 1.3 pts. by wt. of 1-amino-2,3-dioxo-piperazine, 1.3 pts. by wt. of 5-methyl-furfural and 7 pts. by vol. of glacial acetic acid are warmed to 90° C. for 10 minutes and then left for 30 minutes at RT. The precipitate is filtered off, washed first with 3 pts. by vol. of glacial acetic acid and then three times with 10 pts. by vol. of ethyl acetate and dried in air. 1.7 pts. by wt. (76.6%) of 1-(5-methyl-furfurylideneamino)-2,3-dioxo-piperazine of decomp. pt. 245°-8° C. are obtained.

IR(KBr): 3196, 3084, 1669, 1182, 1094, and 787 cm⁻¹.

NMR(d₆DMSO): s (broad) 8.75 (N—H), s 8.45 (1H), d 6.85 (I=3 Hz, 1H), d 6.28 (I=3 Hz, 1H), A B 3.90 and 3.52 (4H), s 2.36 (3H), ppm (δ).

Mass spectrum: m/e 221

Molecular weight: 221.2 calculated: C 54.29; H 5.12; N 19.00. found: C 54.0; H 5.0; N 19.9.

EXAMPLE 6

1-(5-Chlorofurfurylideneamino)-2,3-dioxo-piperazine 1.6 pts. by wt. of 5-chloro-furfural, 1.3 pts. by wt. of 1-amino-2,3-dioxo-piperazine and 7 pts. by vol. of glacial acetic acid are warmed to 90° C. for 10 minutes and then left for 30 minutes at RT. The precipitate is filtered off, washed first with 3 pts. by vol. of glacial acetic acid and then twice with 10 pts. by vol. of acetonitrile each time and dried in air. 1.8 pts. by wt. (74.6%) of 1-(5-chloro-furfurylidene-amino)-2,3-dioxo-piperazine are obtained as yellowish crystals of decomp. pt. 233°-6° C.

IR(KBr): 3202, 3095, 1679, 1484, 1399, 1350, 1199, 1184, 1091, 954 and 783 cm⁻¹.

NMR(d₆—DMSO): s (broad) 8.76 (N—H), s 8.46 (1H), AB 7.16 and 6.72 (I=3 Hz, 2H), A₂B₂ 3.96 and 3.53 (4H) ppm (δ).

Mass spectrum: m/e 241

Molecular weight: 241.6 calculated: C 44.74; H 3.34; N 17.40. found: C 44.7; H 3.3; N 17.4.

EXAMPLE 7

1-(5-Bromofurfurylideneamino)-2,3-dioxo-piperazine 1.9 pts. by wt. of 5-bromofurfural, 1.3 pts. by wt. of 1-amino-2,3-dioxo-piperazine and 7 pts. by vol. of glacial acetic acid were warmed to 90° for 10 minutes and then left for 30 minutes at RT. The precipitate is filtered off, washed with 3 pts. by vol. of glacial acetic acid and recrystallised from dimethylformamide, with the addition of animal charcoal. 1.1 pts. by wt. (38.5%) of 1-(5-bromofurfurylideneamino)-2,3-dioxo-piperazine are obtained as yellowish crystals of decomp. pt. 220°.

IR(KBr): 3205, 3092, 1675, 1471, 1437, 1360, 1347, 1197, 1182, 1091, 952 and 784 cm⁻¹.

NMR(d₆DMSO): s (broad) 8.75 (N—H), s 8.30 (1H), AB 7.06 and 6.84 (I=3 Hz, 2H), A₂B₂ 3.97 and 3.50 (4H) ppm (δ)

Mass spectrum: m/e 285, 287 calculated: C 37.78; H 2.82; N 14.69. found: C 37.7; H 2.8; N 14.5.

It will be appreciated that the instant specification and example set forth by way of illustration and not limitation, and that various modifications and changes may be made without departing from the spirit and scope of the present invention.

What is claimed is:

1. A compound of the formula

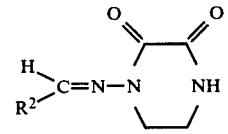

in which R² is a straight-chain or branched alkyl radical with 1 to 6 carbon atoms, a phenyl radical, a phenyl radical which is substituted by halogen, alkyl with 1 to 4 carbon atoms, alkyoxy with 1 to 4 carbon atoms, nitro, cyano, hydroxyl, alkylsulphonyl with 1 to 4 carbon atoms, or methoxycarbonyl, or a furyl, thienyl or isoxazolyl radical, or a furyl, thienyl or isoxazolyl radical which is substituted by halogen or alkyl with 1 to 4 carbon atoms.

2. A compound according to claim 1, wherein such compound is 1-benzylideneamino-2,3-dioxo-piperazine of the formula

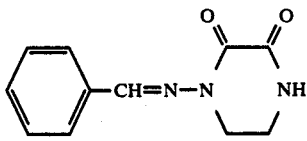

3. A compound according to claim 1, wherein such compound is 1-thienylideneamino-2,3-dioxo-piperazine of the formula

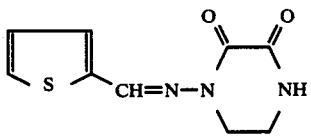

4. A compound according to claim 1, wherein such compound is 1-furfurylideneamino-2,3-dioxo-piperazine of the formula

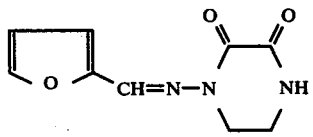

5. A compound according to claim 1, wherein such compound is 1-(5-methylfurfurylideneamino)-2,3-dioxo-piperazine of the formula

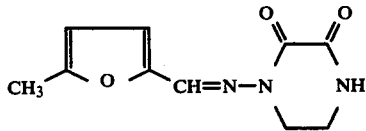

6. A compound according to claim 1, wherein such compound is 1-(5-bromofurfurylideneamino)-2,3-dioxo-piperazine of the formula

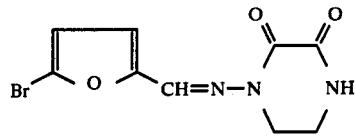

7. A compound according to claim 1, wherein such compound is 1-(5-chlorofurfurylideneamino)-2,3-dioxo-piperazine of the formula

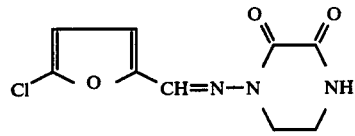

8. A process for the preparation of a compound according to claim 1, comprising reacting a compound of the formula

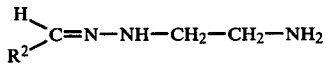

with an oxalic acid ester in the presence of a diluent, thereby to effect cyclization.

9. A pharmaceutical composition for combating viral diseases in human and non-human animals containing as an active ingredient about 0.1 to 99.5% by weight of a compound according to claim 1 in admixture with a pharmaceutically acceptable diluent.

10. A pharmaceutical composition according to claim 9 in the form of a sterile or isotonic aqueous solution.

11. A composition according to claim 9 in the form of a unit dose.

12. A method of combating viral diseases in human and non-human animals which comprises administering to the animals about 1 to 500 mg/kg of body weight per day of a compound according to claim 1.

* * * * *